(12) United States Patent
Herve

(10) Patent No.: US 10,229,091 B2
(45) Date of Patent: Mar. 12, 2019

(54) METHOD FOR RECONSTRUCTING THE OPTICAL PROPERTIES OF A MEDIUM WITH COMPUTING OF A SIGNAL CORRECTED AS A FUNCTION OF A FIRST MODELING FUNCTION FOR A REFERENCE MEDIUM AND OF A SECOND DISTRIBUTION FOR A MEDIUM TO BE CHARACTERIZED, AND ASSOCIATED RECONSTRUCTION SYSTEM

(71) Applicant: Commissariat a l'energie atomique et aux energies alternatives, Paris (FR)

(72) Inventor: Lionel Herve, Corenc (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 1089 days.

(21) Appl. No.: 13/714,912

(22) Filed: Dec. 14, 2012

(65) Prior Publication Data

US 2013/0158926 A1    Jun. 20, 2013

(30) Foreign Application Priority Data

Dec. 16, 2011 (FR) .................................... 11 61835

(51) Int. Cl.
| | |
|---|---|
| *A61B 5/00* | (2006.01) |
| *G01N 21/47* | (2006.01) |
| *G01N 21/64* | (2006.01) |
| *G06F 17/10* | (2006.01) |

(52) U.S. Cl.
CPC ............ *G06F 17/10* (2013.01); *A61B 5/0071* (2013.01); *G01N 21/4795* (2013.01); *G01N 21/645* (2013.01); *G01N 21/6428* (2013.01)

(58) Field of Classification Search
CPC .......... G01N 21/6456; G01N 21/6458; G01N 21/646; A61B 6/582; A61B 6/583
(Continued)

(56) References Cited

U.S. PATENT DOCUMENTS

| 2004/0082070 A1* | 4/2004 | Jones | ................... | A61B 5/0075 436/8 |
|---|---|---|---|---|
| 2007/0238957 A1* | 10/2007 | Yared | ................... | A61B 5/0059 600/407 |

(Continued)

FOREIGN PATENT DOCUMENTS

| EP | 1884765 A1 | 2/2008 |
|---|---|---|
| EP | 2302362 A1 | 3/2011 |
| FR | 2950241 A1 | 3/2011 |
| WO | 2011/032840 A1 | 3/2011 |

OTHER PUBLICATIONS

Arridge S R: "Optical tomography in medical imaging", Inverse problems, Institute of Physics Publishing, Bristol, GB, No. 15, Jan. 1, 1999, pp. R41-R93, XP002404811, ISSN: 0266-5611.

(Continued)

*Primary Examiner* — Michael J Dalbo
(74) *Attorney, Agent, or Firm* — Troutman Sanders LLP

(57) ABSTRACT

A method reconstructing optical properties of a medium uses a reconstruction system having a radiation source illuminating a medium and a detector receiving a signal emitted by the medium. This method includes establishing, for a source-detector pair, a first distribution of a signal received by the detector for a reference medium, the received signal emitted by the reference medium subsequent to the illumination of the medium by the source, determining, for the source-detector pair, a first modeling function of a light scattering signal between the source and the detector in the reference medium, establishing, for the source-detector pair, a second distribution of a signal received by the detector for the medium, the received signal being emitted by the (Continued)

medium to be characterized subsequent to illumination of said medium by the source, and computing a signal corrected as a function of the first modeling function and of the second distribution.

17 Claims, 2 Drawing Sheets

(58) Field of Classification Search
  USPC .................................................... 702/28, 85
  See application file for complete search history.

(56) References Cited

U.S. PATENT DOCUMENTS

| | | | |
|---|---|---|---|
| 2008/0067420 A1* | 3/2008 | Laidevant et al. ......... | 250/459.1 |
| 2010/0224797 A1 | 9/2010 | Laidevant et al. | |
| 2011/0028806 A1* | 2/2011 | Merritt et al. ............... | 600/316 |
| 2011/0042580 A1* | 2/2011 | Wilson .............. | G01N 21/6456 |
| | | | 250/458.1 |
| 2011/0068280 A1* | 3/2011 | Herve et al. .............. | 250/459.1 |
| 2013/0100439 A1* | 4/2013 | Yu ....................... | G01N 21/255 |
| | | | 356/73 |

OTHER PUBLICATIONS

French Search Report and Written Opinion, dated Aug. 10, 2012, which issued during the prosecution of French Patent Application No. 1161835.

\* cited by examiner

METHOD FOR RECONSTRUCTING THE OPTICAL PROPERTIES OF A MEDIUM WITH COMPUTING OF A SIGNAL CORRECTED AS A FUNCTION OF A FIRST MODELING FUNCTION FOR A REFERENCE MEDIUM AND OF A SECOND DISTRIBUTION FOR A MEDIUM TO BE CHARACTERIZED, AND ASSOCIATED RECONSTRUCTION SYSTEM

CROSS-REFERENCE TO RELATED APPLICATION

This application claims priority to French Patent Application No. 11 61835, filed Dec. 16, 2012. The priority application is incorporated herein in its entirety.

FIELD OF THE INVENTION

The present invention concerns a method for reconstructing optical properties of a medium using a reconstruction system comprising at least one radiation source capable of illuminating a medium and at least one detector capable of receiving a signal emitted by the medium.

BACKGROUND

A method and a system of the aforementioned type are known from document EP 2 302 362 A1. The method is intended to locate one or more fluorophores contained in a scattering medium by illuminating the scattering medium with a radiation source and detecting, for at least one detector, the signal emitted by the medium at the fluorescence wavelength. Time distribution of the signal received by the detector is then performed for each source-detector pair.

This time distribution is particularly dependent on the values of the mean response time of the source function $T_s$ and on the mean response time of the detector $T_d$ for each source-detector pair, and it is then necessary to know said values in order to locate the fluorophore(s). The mean time values of the source function $T_s$ and the mean response time values of the detector $T_d$ are measured during a calibration operation in which the source is positioned facing the detector without any scattering medium.

More generally, the time distribution measured using the reconstruction system corresponds to the true time distribution convoluted by an instrument response known as Instrument Response Function—IRF. Instrument response represents the time distribution of the pulse generated by the radiation source and detected by the detector when there is no scattering medium. It is then necessary to measure the instrument response so that it is possible subsequently to determine the true time distribution.

However, the determining of instrument response for each source-detector pair requires lengthy, tedious experimental measurements.

It is therefore an objective of the invention to propose a reconstruction method and a reconstruction system allowing the reconstruction of the desired optical properties of the medium whilst not requiring any experimental determination of instrument response.

SUMMARY

To this end, the subject-matter of the invention is a method for reconstructing the optical properties of a medium wherein it includes:

establishing, for at least one source-detector pair, a first distribution of a signal received by the corresponding detector for a reference medium, the received signal being emitted by the reference medium further to illumination of said medium by the corresponding source;

determining, for said at least one source-detector pair, a first modeling function of a light scattering signal between the source and the detector in the reference medium;

establishing, for said at least one source-detector pair, a second distribution of a signal received by the corresponding detector for a medium to be characterized, the received signal being emitted by the medium to be characterized further to illumination of said medium by the corresponding source; and computing a corrected signal, corrected as a function of the first modeling function and the second distribution.

By reconstruction of the optical properties is meant for example:

the reconstruction of absorption properties, these being characterized in particular by the absorption coefficient denoted $\mu_a$.

the reconstruction of scattering properties, these being characterized in particular by the reduced scattering coefficient $\mu'_s$ or by the scattering coefficient D.

the reconstruction of fluorescence properties, these being characterized in particular by a response function F of a fluorophore, or by a concentration c of a fluorophore, or by any other magnitude expressing a quantity q of a fluorophore, the latter being endogenous or exogenous for example.

The reconstruction of the optical properties allows the determination of the spatial distribution of optical coefficients such as those described above, well known in the field of optical scatter imaging. It is a two- or three-dimensional reconstruction.

According to other advantageous aspects of the invention, the reconstruction method comprises one or more of the following characteristics taken alone or in any possible technical combination:

the computing of the corrected signal is also performed according to the first distribution, the method further includes the determining, for said at least one source-detector pair, of a second modeling function of a light scattering signal between the source and the detector in the medium to be characterized, and the corrected signal is also computed according to the second modeling function;

the computing step comprises an operation to compare the product of the first distribution and the second modeling function with the product of the second distribution and first modeling function;

the comparison operation comprises an arithmetical operation of the product of the first distribution and the second modeling function with the product of the second distribution and the first modeling function;

the arithmetical operation is a subtraction of the product of the first distribution and the second modeling function from the product of the second distribution and the first modeling function;

the arithmetical operation is a ratio between the product of the second time distribution and the first modeling function and the product of the first time distribution and the second modeling function;

the first and second distributions are time distributions, and the product of the first distribution and second modeling function and the product of the second distribution and first modeling function are convolution products;

the first and second distributions are continuous distributions, and the product of the first distribution and the second modeling function and the product of the second distribution and the first modeling function are multiplications;

the first and second distributions are frequency distributions, and the product of the first distribution and the second modeling function and the product of the second distribution and the first modeling function are multiplications;

the first distribution is established for an excitation wavelength, the second distribution is established for an emission wavelength, and the corrected signal is expressed as a function of the product of a positive scalar and the first time distribution, the product of the second distribution and the first modeling function being a function of the product of the positive scalar and the first time distribution, the positive scalar being equal to the ratio between an instrument response corresponding to detection performed at the emission wavelength and an instrument response corresponding to detection performed at the excitation wavelength, and the optical properties comprise at least one element from among the group of:
the absorption properties of light, characterized in particular by the absorption coefficient,
the scattering properties, characterized in particular by the reduced scattering coefficient or by the scattering coefficient, and
the fluorescence properties, characterized in particular by a response function of a fluorophore, or by a concentration of the fluorophore, or by a magnitude that is function of a quantity of the fluorophore.

A further subject of the invention is a reconstruction system having
at least one radiation source capable of illuminating a medium,
at least one detector capable of receiving a signal emitted by the medium,
means for establishing, at least for one source-detector pair, a first distribution of a signal received by the corresponding detector for a reference medium, the received signal being emitted by the reference medium subsequent to illumination of said medium by the corresponding source,
first means for determining, for said at least one source-detector pair, a first modeling function of a light scattering signal between the source and the detector in the reference medium;
means for establishing, for said at least one source-detector pair, a second distribution of a signal received by the corresponding detector for a medium to be characterized, the received signal being emitted by the medium to be characterized subsequent to illumination of said medium by the corresponding source; and
means for computing a signal corrected as a function of the first modeling function and of the second distribution.

According to other advantageous aspects of the invention, the reconstruction system has one or more of the following characteristics taken alone or in any technically possible combination:

the computing means are capable of computing the corrected signal also according to the first distribution;
the system further comprises second determination means, for said at least one source-detector pair, to determine a second modeling function of a light scattering signal between the source and the detector in the medium to be characterized, and the corrected signal is also computed according to the second modeling function.

BRIEF DESCRIPTION OF THE DRAWINGS

These characteristics and advantages of the invention will become apparent on reading the following description given solely as an example and with reference to the appended drawings in which.

DETAILED DESCRIPTION

Figure 1:
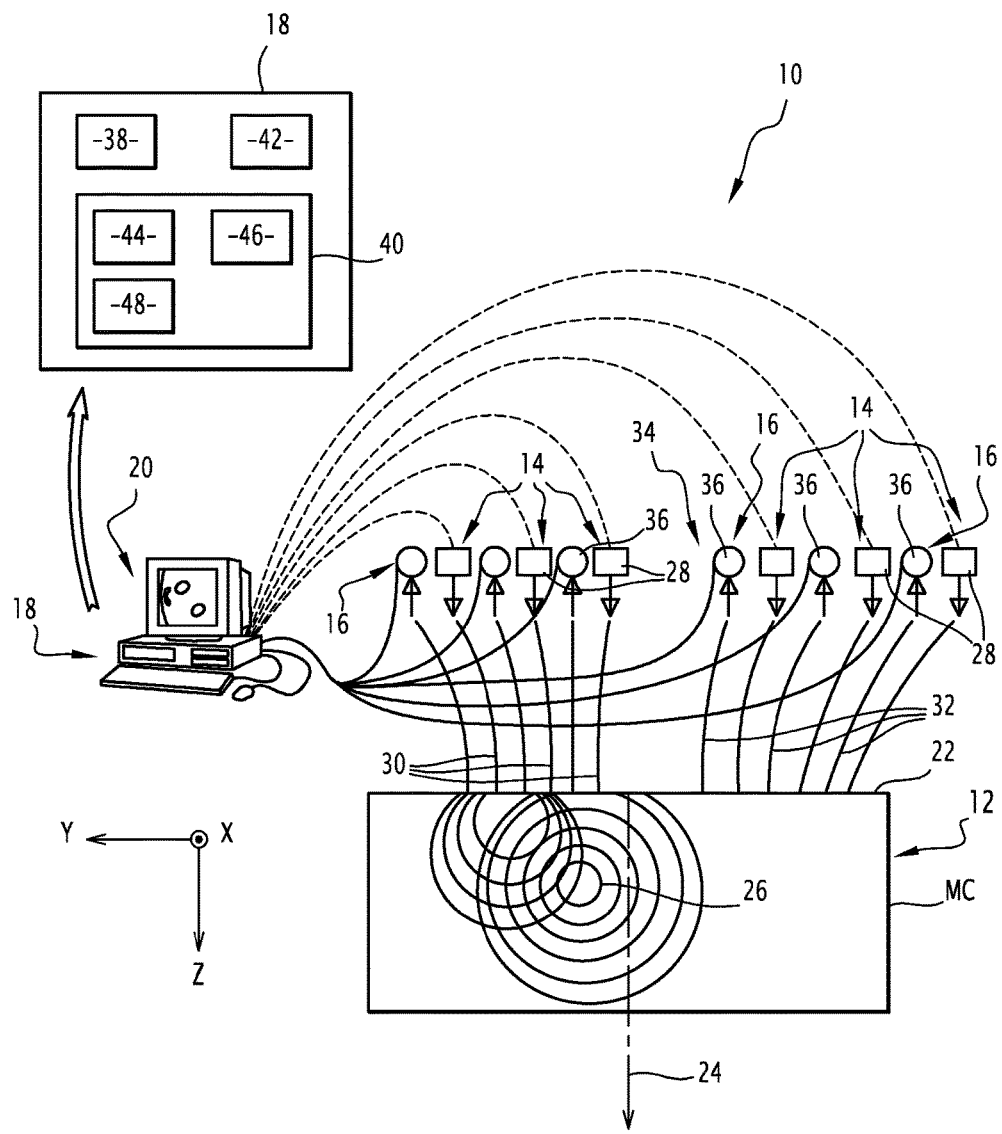
FIG. 1 is a schematic illustration of a reconstruction system according to an example of the invention.

In FIG. 1, a reconstruction system 10 is intended to perform examination of a medium 12 via the acquisition of an image of the medium 12, followed by processing of this image.

The reconstruction system 10 comprises a plurality of radiation sources 14 capable of illuminating the medium 12 and a plurality of detectors 16 capable of receiving a signal emitted by the medium 12. The radiation sources 14 and the detectors 16 are arranged for example in a probe, not illustrated.

The system 10 comprises a data processing unit 18 and a display screen 20 to display an image of the medium.

In the described embodiment, the system 10 is a time system, and each radiation source 14 is a pulsed radiation source. Each detector 16 is a time-resolved detector i.e. a detector allowing the measurement of the time distribution of photon arrival time. The detector 6 is a device of TCSPC type for example (Time-Correlated Single Photon Counting).

In the illustrated example, the medium 12 has an observation surface 22 in the form of a plane parallel to a longitudinal axis X and a transverse axis Y against which the sources 14 and detectors 16 can be applied. The medium 12 has an observation direction 24 extending along a vertical axis Z and substantially perpendicular to the observation surface 22.

During a first phase, the medium 12 is a reference medium denoted MR, not illustrated, also known as a phantom. The reference medium MR is known per se and is described for example in document FR 2 950 241 A1.

The MR phantom has known optical characteristics, preferably close to within a few ten percentages e.g. 50% even to within 30% of those of a medium to be characterized denoted MC, and which it is desired to examine. The phantom MR is a phantom for example having coefficients of absorption $\mu_a^0$ and scattering $D^0$ that are homogeneous and of median values for human tissues, for example of 0.2 $cm^{-1}$ and 10 $cm^{-1}$ respectively.

During a second phase, the medium 12 is the medium to be characterized MC which can be seen in FIG. 1. The medium to be characterized MC includes biological tissues of an animal or of man. The medium to be characterized MC is a region of an organ such as the brain for example or a breast, prostate, digestive tract or other organ into which fluorophores can be injected. More generally, the medium to be characterized MC is a biological medium, for example an organ for which it is desired to determine optical scattering properties and in particular the spatial distribution of coefficients such as the absorption coefficient or the scattering coefficient.

In the example in FIG. 1, the medium to be characterized MC is a scattering medium containing inclusions 26 having different optical absorption or scattering properties from those of the reference medium MR. Only one inclusion 26 is illustrated in FIG. 1 for reasons of clarity of the drawing. Therefore, by mapping the absorption coefficient $\mu_a$ and the scattering coefficient D, their heterogeneities can be located which allows the locating of the inclusions.

Each pulsed radiation source 14 has a pulsed light source 28 and an excitation optical fiber 30 connected to the pulsed source 28 for transmission of the light pulse as far as the medium 12. When a said fiber source is used, the free end of the excitation fiber 30 is likened to the source s.

As a variant, not illustrated, each pulsed radiation source 14 comprises an excitation optical fiber 30 connected to a single pulsed light source common to the plurality of radiation sources 14. According to this variant, the system 10 further comprises an optical switch or multiplexer to select the excitation fiber 30 into which the light beam is sent.

As a further variant, all the pulsed radiation sources 14 are formed of a single pulsed light source and of a mirror device of MEMS type (MicroElectroMechanical Systems), not illustrated, to scan the medium 12 with the light derived from the pulsed light source. As another variant, the source 14 is a multiplexed source delivering light pulses at different wavelengths.

When examining the surface 22 of the medium or when examining at shallow depth in the medium 12, i.e. at a depth of a few millimeters, the wavelength of each pulsed radiation source 14 is preferably in the near infrared or visible i.e. between 500 nm and 1300 nm. The repeat rate is about 50 MHz.

The pulses emitted by each pulsed radiation source 14 have a time length of between 500 picoseconds and 50 femtoseconds, each pulsed light source 28 being capable of generating a pulse having a time length of between 500 picoseconds and 50 femtoseconds.

Each time-resolved detector 16 includes a detecting optical fiber 32 connected to a time-resolved detection module 34. The free end of this detecting optical fiber 32 is likened to the detector d.

In the example in FIG. 1, the detection module 34 has a detection member 36 for each detector 16. As a non-illustrated variant, the detection module 34 includes a detection member common to several detectors 16, in particular a single detection member for all the detectors 16.

The detection member 36 is a photomultiplier for example, or an avalanche photodiode (APD) or a single-photon avalanche photodiode (SPAD) or an image intensifying tube having one or more anodes (Multi-Channel Plate).

The probe is a compact probe for diagnosing some cancers, such as a portable probe for diagnosing breast cancer, an endorectal probe for diagnosing prostate cancer, or a dermatological probe. As a variant, the probe is an endoscopic probe such as a flexible probe for diagnosing digestive cancer.

The data processing unit 18 includes a data processor 38 and a memory 40 associated with the processor 38.

The processing unit 18 has means 42 for establishing, for at least one source 14/detector 16 pair, a first distribution $A_{sd}$ of a signal received by the corresponding detector 16 for the reference medium MR during the first phase, the received signal being emitted by the reference medium MR subsequent to illumination of said medium MR by the corresponding source 14, and a second distribution $B_{sd}$ of a signal received by the corresponding detector 16 for the medium to be characterized MC during the second phase, the received signal being emitted by the medium to be characterized MC subsequent to illumination of said medium MC by the corresponding source 14.

In the described example, the first and second distributions are time distributions respectively denoted $A_{sd}(t)$ and $B_{sd}(t)$. The establishing means 42 are preferably in the form of one or more electronic cards connected to the detector 16 allowing measurement of the time distribution of photon arrival time.

Each pulsed light source 28 has a pulsed laser. As a variant, each pulsed light source 28 includes a laser diode. As a further variant, each pulsed light source 28 includes a constant light source whose light intensity is modulated to pulses of equivalent duration by a fast shutter device. Therefore, according to this first embodiment, the source is capable of emitting light radiation assuming the form of a time pulse.

The end of each excitation fiber 30 extends perpendicular to the observation surface 22 i.e. along axis Z, or obliquely to axis Z to emit light obliquely relative to the observation surface 22.

The memory 40 is capable of storing a first determination software program 44 for said at least one source 14/detector 16 pair, to determine a first modeling function $G_{sd}^0$ of a light scattering signal between the source 14 and the detector 16 in the reference medium MR. The memory 40 is capable of storing computing software 46 to compute a signal corrected as a function of the first distribution, of the first modeling function and of the second distribution.

The memory 40 is capable of storing second software 48 to determine, for said at least one source 14/detector 16 pair, a second modeling function $G_{sd}$ of a light scattering signal between the source 14 and the detector 16 in the medium to be characterized MC. The computing software 46 is then capable of computing the corrected signal also as a function of the second modeling function.

As a variant, the first determination means 44, the computing means 46 and the second determination means 48 are in the form of programmable logical components or in the form of dedicated integrated circuits.

The first and second modeling functions $G_{sd}^0$, $G_{sd}$ are Green functions for example, well known in the field of medical imaging. Each Green function $G_{sd}^0$, $G_{sd}$ represents photon density at the detector 16 when the medium 12 i.e. the reference medium MR for the first modeling function and respectively the medium to be characterized MC for the second modeling function, is illuminated by the source 14, where the subscripts s and d respectively designate the source 14 and the detector 16.

The first time distribution $A_{sd}(t)$ then verifies the following equation:

$$A_{sd}(t) = IRF_{sd}(t) * G_{sd}^0(t) \quad (1)$$

where $IRF_{sd}(t)$ is the instrument response i.e. the influence of the source s and of the detector d on the first established distribution.

The second time distribution $B_{sd}(t)$ verifies the following equation:

$$B_{sd}(t) = IRF_{sd}(t) * G_{sd}(t) \quad (2)$$

In the described example, the first and second modeling functions and the corrected signal are respectively denoted $G_{sd}^0(t)$, $G_{sd}(t)$ and $Y_{sd}(t)$.

The computing software 46 is capable of performing a comparison operation of the product of the first distribution $A_{sd}$ and of the second modeling function $G_{sd}$ with the product of the second distribution $B_{sd}$ and of the first modeling function $G_{sd}^0$. The comparison operation has an arithmetical operation of the product of the first distribution $A_{sd}$ and second modeling function $G_{sd}$ with the product of the second distribution $B_{sd}$ and first modeling function $G_{sd}^0$.

The arithmetical operation is a subtraction for example of the product of the first distribution $A_{sd}$ and second modeling function $G_{sd}$ from the product of the second distribution $B_{sd}$ and first modeling function $G_{sd}^0$.

In the described example the product of the first distribution $A_{sd}(t)$ and of the second modeling function $G_{sd}(t)$ and the product of the second distribution $B_{sd}(t)$ and of the first modeling function $G_{sd}^0(t)$ are convolution products, the first $A_{sd}(t)$ and second $B_{sd}(t)$ distributions being time distributions.

The corrected signal $Y_{sd}(t)$ verifies the following equation:

$$Y_{sd}(t) = B_{sd}(t) * G_{sd}^0(t) - A_{sd}(t) * G_{sd}(t) \quad (3)$$

where $B_{sd}(t)$ is the second time distribution,
$G_{sd}^0(t) = G_s^0(r_d, t) = G^0(r_s, r_d, t)$ is a Green function representing photon density at time t, at the detector located at $r_d$, when the reference medium is illuminated by a source s located at $r_s$, this function being called a first modeling function;
$G_{sd}(t) = G_s(r_d, t) = G(r_s, r_d, t)$ is a Green function representing photon density at time t at the detector located at $r_d$, when the examined medium is illuminated by a source s located at $r_s$, this function being called a second modeling function; and
$A_{sd}(t)$ is the first time distribution.

As a variant, the arithmetical operation is a ratio between the product of the second time distribution and the first modeling function and the product of the first time distribution and the second modeling function.

According to this variant, the corrected signal $Y_{sd}(t)$ then verifies the following equation:

$$Y_{sd}(t) = \frac{B_{sd}(t) * G_{sd}^0(t)}{A_{sd}(t) * G_{sd}(t)} \quad (4)$$

Figure 2:
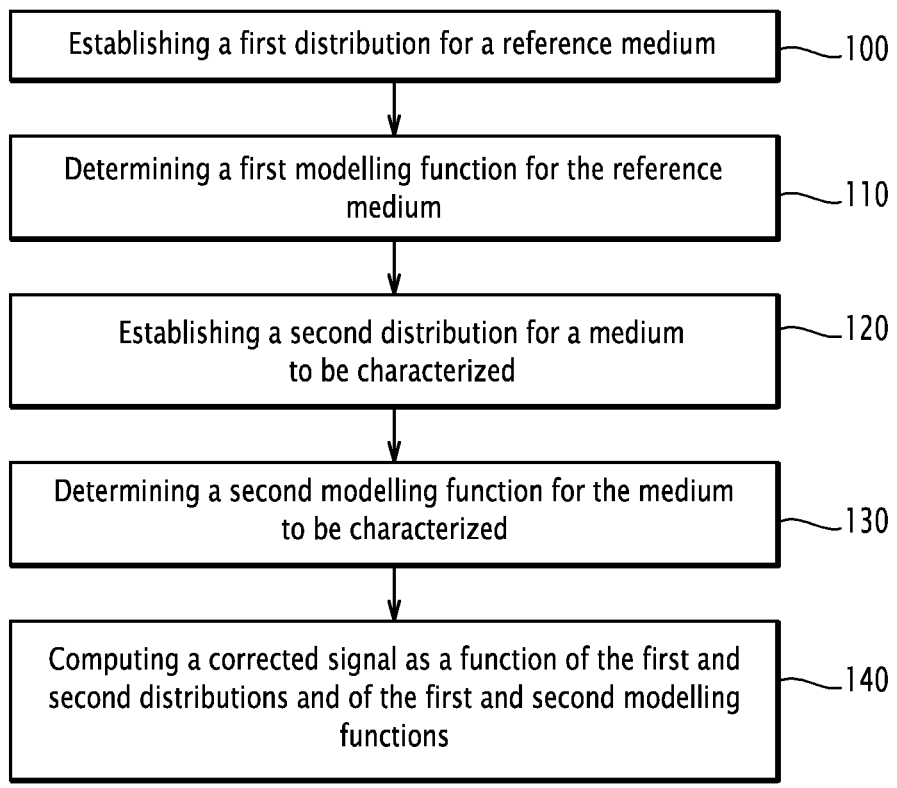
FIG. 2 is a flow chart of a reconstruction method according to an example of the invention.

The operation of the reconstruction system 10 according to the invention is described below with the help of FIG. 2 illustrating a flow chart of the image processing method according to an example of the invention.

Initially at step 100, the reference medium MR also called a phantom is illuminated by the corresponding source(s) 14. If there is a plurality of sources 14, the illumination of the medium 12 is successively performed by each of the sources 14. When it is illuminated, the reference medium MR in turn emits a light signal towards the or each detector 16, and the first distribution of the received signal $A_{sd}(t)$ is established for each source 14/detector 16 pair, also denoted (s, d), by means of the establishing means 42.

At step 110, the reconstruction system 10 then determines via the first determination means 44 and for each source/detector pair (s, d), the first modeling function $G_{sd}^0(t)$ of the light scattering signal between the source 14 and the detector 16 in the reference medium MR.

Steps 100 and 110 correspond to the first phase performed on the reference medium MR.

An operator then changes the medium 12 and replaces the reference medium MR by the medium to be characterized MC so that the reconstruction system 10 performs the following steps of the image processing method.

The medium to be characterized MC is first illuminated by the corresponding source(s) 14 (step 120). When it is illuminated, the medium to be characterized MC in turn emits a light signal towards the or each detector 16, and the second distribution of the received signal $B_{sd}(t)$ is established for each source-detector pair (s, d), by the establishing means 42.

At step 130, the reconstruction system 10 then determines via the second determination means 48 and for each source-detector pair (s, d), the second modeling function $G_{sd}(t)$ of the light scattering signal between the source 14 and the detector 16 in the medium to be characterized MC.

The corrected signal $Y_{sd}(t)$ is then computed at step 140 by the computing means 46, as a function of the first distribution $A_{sd}(t)$, of the first modeling function $G_{sd}^0(t)$, of the second distribution $B_{sd}(t)$ and of the second modeling function $G_{sd}(t)$. The corrected signal $Y_{sd}(t)$ verifies preceding equation (3) for example.

In addition, the second modeling function $G_{sd}(t)$ is approximately determined using the Green function $G_{sd}^1(t)$ for the medium to be characterized. The reconstruction process of the optical properties is generally iterative so that, at each iteration, values $\mu_a^1(r)$ and $D^1(r)$ are obtained to which Green functions $G_{sd}^1(t)$ correspond for each source-detector pair (s, d).

The iterative process then verifies the following equations:

$$\begin{aligned}Y_{sd}(t) &= B_{sd}(t) * G_{sd}^0(t) - A_{sd}(t) * G_{sd}^1(t) \quad (5)\\ &= IRF_{sd}(t) * G_{sd}(t) * G_{sd}^0(t) - IRF_{sd}(t) * G_{sd}(t) * G_{sd}^1(t)\\ &= IRF_{sd}(t) * G_{sd}^0(t) * (G_{sd}(t) - G_{sd}^1(t))\\ &= A_{sd}(t) * (G_{sd}(t) - G_{sd}^1(t))\\ &\approx -A_{sd}(t) * \begin{pmatrix} \int G_s^1(\vec{r}, t) * \delta\mu_a(\vec{r}, t) * G_d^1(\vec{r}, t) d\vec{r} + \\ \int \vec{\nabla} G_s^1(\vec{r}, t) * \delta D(\vec{r}, t) * \vec{\nabla} G_d^1(\vec{r}, t) d\vec{r} \end{pmatrix}\end{aligned}$$

where $\mu_a$ and D respectively represent the absorption coefficient and the scattering coefficient of the medium to be characterized MC,
$IRF_{sd}$ is the instrument response corresponding to the source-detector pair used,
$G_s(r,t) = G(r_s,r,t)$ is the Green function representing photon density at a point r of the medium MC when the medium MC is illuminated by the source s located at $r_s$,
$G_d(r,t) = G(r_d,r,t)$ is the Green function representing photon density at point r of the medium MC when the medium MC is illuminated by the source s located at $r_d$. This Grren function is also written $G_d(r,t) = G(r,r_d,t)$. Therefore this Green function also represents photon density at the detector ($r_d$) when the medium is illuminated by a source located at r.

In other words, $G_{sd}(t)$ corresponds to the true values $\mu_a(r, t)$ and $D(r, t)$, i.e. to the sought after values, and $G_{sd}^1(t)$ corresponds to approximated values $\mu_a^1(r, t)$ and $D^1(r, t)$ with $\mu_a^1(r, t) = \mu_a(r, t) + \delta\mu_a(r, t)$ and $D^1(r, t) = D(r, t) + \delta D(r, t)$. The objective of the reconstruction method is then to minimize o δμ$_a$(r, t) and δD(r, t), which makes it possible to cause μ$^1$(r, t) and D$^1$(r, t) to tend towards μ$_a$(r, t) and D(r, t) respectively.

The coefficients μ$_a$ and D are constant over time, and the values μ$_a$(r, t) and D(r,t) are written μ$_a$(r, t)=μ$_a$(r)∂(t) and D(r,t)=D(r)∂(t), with ∂(t) representing a Dirac distribution at time t.

The computing of the corrected signal Y$_{sd}$(t), also called the corrected time distribution, therefore overcomes the need for precise knowledge of the instrument response IRF$_{sd}$(t) according to equations (3), (4) or even (5). This makes it possible to avoid lengthy, tedious experimental measurements used in the prior art method in order to determine the instrument response of the reconstruction system 10.

The corrected signal Ysd(t) is then used in conventional reconstruction methods of the optical scattering signal. For example, these methods use time distribution transforms Ysd(t), such as Mellin transforms or Mellin-Laplace transforms. After a meshing step of the medium to be characterized MC in voxels, a linear system is obtained relating:
- the measured magnitudes, for example comprising Mellin or Mellin-Laplace transforms Ysd(t);
- modeled magnitudes namely transforms of the Green functions; and
- the unknowns, δμ$_1$($\vec{r}_m$, t) and δD($\vec{r}_m$, t), the subscript m representing the centre voxel r$_m$.

The transforms of the corrected distribution Ysd, such as the Mellin-Laplace transforms Y$_{sd}^{(p,n)}$, are computed for different values of order n of between 0 and n$_{max}$, preferably for all the successive values between 0 and n$_{max}$, according to the following equation:

$$Y_{sd}^{(p,n)} = \sum_{i+j=n} \left( B_{sd}^{(p,i)} \cdot G_{sd}^{0(p,j)} - A_{sd}^{(p,i)} \cdot G_{sd}^{(p,j)} \right) \quad (6)$$

However, the corrected distribution Y$_{sd}$(t) verifies the following equation:

$$Y_{sd}(t) = -A_{sd}(t) * (\int G_s^1(\vec{r},t) * \delta\mu_a(\vec{r},t) * G_d^1(\vec{r},t) d\vec{r} + \int \vec{\nabla} G_s^1(\vec{r},t) * \delta D(\vec{r},t) * \vec{\nabla} G_d^1(\vec{r},t) d\vec{r}) \quad (7)$$

The equations (6) and (7) then allow the following equation to be obtained since the Mellin-Laplace transform of a convolution product of two terms is equal to the product of the Mellin-Laplace transforms of each of these two terms:

$$Y_{sd}^{(p,n)} = -\sum_{i+j+k=n} A_{sd}^{(p,k)} \cdot \left( \int G_s^{1(p,i)}(\vec{r}) \cdot \delta\mu_a(\vec{r}) \cdot G_d^{1(p,j)}(\vec{r}) d\vec{r} + \int \vec{\nabla} G_s^{1(p,i)}(\vec{r}) \cdot \delta D(\vec{r}) \cdot \vec{\nabla} G_d^{1(p,j)}(\vec{r}) \cdot d\vec{r} \right) \quad (8)$$

The equation (8) can therefore be used to calculate the n-order Mellin-Laplace transform of the corrected distribution Y$_{sd}^{(p,n)}$ of the Mellin-Laplace transforms of the first time distribution A$_{sd}$(t) and of the Green functions G$_s^1$(r), G$_d^1$(r) approximating the second modeling function G$_{sd}$(t).

The medium 12 is discretised into a plurality M of voxels referenced m, where m is between 1 and M, in order to calculate the Mellin-Laplace transforms of the Green functions G$_s^1$(r), G$_d^1$(r). The Green functions G$_s^1$(r), G$_d^1$(r) discretised for each voxel m are denoted G$_s^1$(r$_m$), G$_d^1$(r$_m$).

The reconstruction of optical properties of the medium 12 is then performed to determine for example the vectors $\vec{\mu}_a$ and $\vec{D}$, whose terms μ$_a$(m) and D(m), discretised for each voxel m, i.e. μ$_a$($\vec{r}=\vec{r}_m$) and D($\vec{r}=\vec{r}_m$), provide the maps of the desired optical properties.

The reconstruction step is then intended to solve the following matrix system:

$$\underline{Y} = \underline{WX}, \quad (9)$$

where $\underline{Y}$ represents a vector of the observations, $\underline{W}$ represents a transition matrix and $\underline{X}$ is a vector of the unknowns.

The vector of observations $\underline{Y}$ contains the Nn Mellin-Laplace transforms of the corrected distribution Y$_{sd}^{(p,n)}$, with Nn equal to n$_{max}$+1, calculated for all the successive values of order n between 0 and n$_{max}$ and for the source—detector pairs (s, d) under consideration.

For each triplet (s, d, n) of indices s, d and of order n, an index I is defined in the following manner:

$$I = (s-1) \times Nd \times Nn + (d-1) \times Nn + n \quad (10)$$

where Nd is the number of detectors 16 under consideration.

The maximum value of the index I is equal to Imax, such that:

$$I_{max} = Ns \times Nd \times Nn \quad (11)$$

The vector of the observations $\underline{Y}$ then comprises Imax lines.

The transition matrix $\underline{W}$ comprises a first part W$^\mu$ comprising first terms denoted W$^\mu$ (I, m) and a second part W$^D$ comprising second terms denoted W$^D$(I, m). This matrix is also called a matrix of the sensitivity of the measurements Y to the optical properties X.

The first terms W$^\mu$ (I, m) verify the following equation:

$$W^\mu(I, m) = -\sum_{i+j+k=n} A_{sd}^{(p,k)} \cdot G_s^{1(p,i)}(\vec{r}_m) \cdot G_d^{1(p,j)}(\vec{r}_m) \cdot V_m \quad (12)$$

and the second terms W$^D$(I, m) verify the following equation:

$$W^D(I, m) = -\sum_{i+j+k=n} A_{sd}^{(p,k)} \cdot \vec{\nabla} G_s^{1(p,i)}(\vec{r}_m) \cdot \vec{\nabla} G_d^{1(p,j)}(\vec{r}_m) \cdot V_m \quad (13)$$

where V$_m$ is a volume element surrounding the mesh m, for example the volume of the Voronoi cell. In other words V$_m$ represents the volume of the voxel m.

According to this embodiment, at each iteration, the Mellin Laplace transforms of different orders of G$_s^1$(t) and G$_d^1$(t) are determined, in particular using the following expression:

$$-\vec{\nabla} D(\vec{r}) \vec{\nabla} G_s^{1(p,n)}(\vec{r}) + \left(\mu_a(\vec{r}) + \frac{p}{c}\right) G_s^{1(p,n)}(\vec{r}) = \begin{cases} \delta(r) \sin = 0 \\ \frac{p}{c} G_s^{1(p,n-1)}(\vec{r}) \sin > 0 \end{cases} \quad (14)$$

Therefore at each iteration G$_s^{1(p,n=0)}$ is determined then the transforms of higher order are determined iteratively using the above expression when n>0. At the first iteration, D=D$^0$ and μ$_a$=μ$_a^0$ are used, and at the following iterations D=D$^1$ and $\mu_a = \mu_a^1$ are used. The same reasoning evidently applies for determining Mellin Laplace transforms of the function $G_d^1(t)$.

The transition matrix $\underline{W}$ then comprises Imax lines and 2M columns.

Each term $W^H(I, m)$, $W^D(I, m)$ of the transition matrix $\underline{W}$ is determined by modeling at each iteration, as a function of the optical properties determined at the preceding iteration, or at the first iteration, in relation to the optical properties initialized by the operator. This initialization is performed giving consideration to a homogeneous medium 12 for example.

The vector of the unknowns $\underline{X}$ comprises 2M lines and one column, and contains the unknowns $\mu_a(m)$ and $D(m)$ for each of the M voxels. The first M lines correspond to the unknowns $\mu_a(m)$ and the M following lines of the vector $\underline{X}$ correspond to the unknowns $D(m)$.

The inverting of the transition matrix $\underline{W}$ is performed using inversion algorithms well known to persons skilled in the art, such as a gradient descent algorithm, an algebraic reconstruction technique (ART), single value decomposition (SVD), or a conjugate gradient method. The process is stopped when a convergence criterion is reached, for example when the distance between two successive vectors $\underline{X}$ is lower than a predetermined threshold.

It can therefore be appreciated that the reconstruction method and the reconstruction system 10 of the invention allow the reconstruction of desired optical properties whilst not requiring any experimental determination of instrument response.

According to one variant of this embodiment, the position of fluorophores in the medium to be characterized MC is reconstructed. For this purpose, a measurement $A_{sd}(t)$ is carried out corresponding to the excitation of the reference medium MR by a wavelength called a reference wavelength and denoted $\lambda_{ref}$. This reference wavelength corresponds to the excitation wavelength of the fluorophore $\lambda_{ex}$. The signal $A_{sd}(t)$ is therefore detected at the excitation wavelength. It is then assumed that the response of the detector $D_d(t)$ undergoes negligible change between the excitation wavelength $\lambda_{ex}$ and the reference wavelength $\mu_{ref}$, or that its trend is controlled, for example by a relationship of proportionality. It is then assumed that the instrument response $IRF_{sd}^{\lambda ex}(t)$ corresponding to the detection performed at the excitation wavelength is related to the instrument response $IRF_{sd}^{\lambda em}(t)$ corresponding to the detection performed at the emission wavelength of the fluorophore, via a relationship of type $IRF_{sd}^{\lambda em}(t) = \alpha IRF_{sd}^{\lambda ex}(t)$, $\alpha$ being a positive scalar.

This measurement is performed on the reference medium MR whose optical properties are known. Preferably, these are close to within a few ten percentages, for example to within 50% of those of the medium to be characterized MC.

$$A_{sd}(t) = IRF_{sd}^{\lambda ex}(t) * G_{sd}^0(t), \quad (15)$$

$G_{sd}^0(t)$ being the Green function corresponding to photon density at $\vec{r} = \vec{r}_d$, in the reference medium MR, when this medium is illuminated by a pulsed source of Dirac type at $\vec{r} = \vec{r}_s$.

Each measurement $B_{sd}(t)$ corresponds to the fluorescence signal, at the emission wavelength $\lambda_{em}$, measured by a detector d located at $r_d$, when the examined medium is excited by an excitation source s, located at $r = r_s$, and delivering a light pulse at the excitation wavelength $\lambda_{ex}$.

Each measurement $B_{sd}(t)$ is modeled in the following manner:

$$B_{sd}(t) = IRF_{sd}^{\lambda em}(t) * \int G_s^{\lambda ex}(\vec{r},t) * F(\vec{r},t) * G_d^{\lambda em}(\vec{r},t) d\vec{r} \quad (16)$$

with:

$G_s^{\lambda ex}(\vec{r}, t)$: Green function corresponding to photon density at $\vec{r}$ when the medium is illuminated by a Dirac pulsed source located at $\vec{r}_s$, $G_d^{\lambda em}(r, t)$: Green function corresponding to photon density at $\vec{r}_d$ when the medium is illuminated by a Dirac pulsed source located at $\vec{r}$, and $F(\vec{r}, t)$: response of the fluorophore located in the volume $d\vec{r}$, $$F(\vec{r}, t) = F(\vec{r})\exp\left(-\frac{t}{\tau}\right)\tau$$

designating the lifetime of the fluorophore. $F(\vec{r})$ is determined using the following equation: $F(\vec{r}) = \mu_a(\vec{r})\eta$, $\eta$ being the fluorescence yield.

The corrected magnitude $Y_{sd}(t)$ is then established, such that $$\begin{aligned} Y_{sd}(t) &= B_{sd}(t) * G_{sd}^0(t) \\ &= IRF_{sd}^{\lambda em}(t) * \int G_s^{\lambda ex}(\vec{r}, t) * F(\vec{r}, t) * \\ & \quad G_d^{\lambda em}(\vec{r}, t) d\vec{r} * G_{sd}^0(t) \\ &= \alpha A_{sd}(t) * \int G_s^{\lambda ex}(\vec{r}, t) * F(\vec{r}, t) * G_d^{\lambda em}(\vec{r}, t) d\vec{r} \end{aligned} \quad (17)$$

The corrected magnitude Ysd(t) is then related to measured or known magnitudes ($\alpha$, $A_{sd}(t)$), to modeled magnitudes $G_s^{\lambda ex}(\vec{r}, t)$, $G_d^{\lambda em}(\vec{r}, t)$, and to the unknowns $F(\vec{r}, t)$. By having several corrected magnitudes, corresponding to different source-detector pairs, the magnitudes $F(\vec{r}, t)$ are reconstructed using known inversion algorithms such as those mentioned previously.

According to another example, in which elements identical to the previously described example carry identical reference numbers and are not described a further time, the reconstruction system 10 is a continuous system.

Each radiation source 14 is a continuous radiation source also called a continuous light source, such as a filtered white source or a monochrome laser source.

Each detector 16 is a continuous detector capable of measuring the attenuation of light intensity. Each continuous detector 16 is an image sensor such as a CCD sensor (Charge-Coupled Device) or a CMOS sensor (Complementary Metal-Oxide Semiconductor). As a variant, each continuous detector 16 is a point detector such as a photomultiplier, a photodiode or an avalanche photodiode.

According to another example, the first and second distributions are continuous distributions respectively denoted $A_{sd}$ and $B_{sd}$. The establishing means 42 are preferably in the form of software which can be stored in the memory 40.

In this example, the first and second modeling functions and the corrected signal are respectively denoted $G_{sd}^0$, $G_{sd}$ and $Y_{sd}$.

According to this example, the product of the first distribution $A_{sd}$ and of the second modeling function $G_{sd}$, and the product of the second distribution $B_{sd}$ and of the first modeling function $G_{sd}^0$ are multiplications, the first $A_{sd}$ and second $B_{sd}$ distributions being continuous distributions.

The arithmetical operation is a subtraction for example of the product of the first continuous distribution $A_{sd}$ and the second modeling function $G_{sd}$ from the product of the second continuous distribution $B_{sd}$ and the first modeling function $G_{sd}^0$.

The corrected signal $Y_{sd}$ verifies the following equation:

$$Y_{sd} = B_{sd} \cdot G_{sd}^0 - A_{sd} \cdot G_{sd} \qquad (18)$$

where $B_{sd}$ is the second continuous distribution,
$G_{sd}^0$ is the first modeling function,
$A_{sd}$ is the first continuous distribution, and
$G_{sd}$ is the second modeling function.

As a variant, the arithmetical operation is a ratio between the product of the second continuous distribution $B_{sd}$ and the first modeling function $G_{sd}^0$, and the product of the first continuous distribution $A_{sd}$ and the second modeling function $G_{sd}$.

According to this variant, the corrected signal $Y_{sd}$ then verifies the following equation:

$$Y_{sd} = \frac{B_{sd} \cdot G_{sd}^0}{A_{sd} \cdot G_{sd}} \qquad (19)$$

In addition the second modeling function $G_{sd}$ is approximately determined using the Green function $G_{sd}^1$ for the medium to be characterized, and the following equations are then obtained:

$$\begin{aligned} Y_{sd} &= B_{sd} \cdot G_{sd}^0 - A_{sd} \cdot G_{sd}^1 \qquad (20) \\ &= IRF_{sd} \cdot G_{sd} \cdot G_{sd}^0 - IRF_{sd} \cdot G_{sd}^0 \cdot G_{sd}^1 \\ &= IRF_{sd} \cdot G_{sd}^0 \cdot (G_{sd} - G_{sd}^1) \\ &= A_{sd} \cdot (G_{sd} - G_{sd}^1) \\ &= -A_{sd} \cdot \left( \begin{array}{l} \int G_s^1(\vec{r}) \cdot \delta\mu_a(\vec{r}) \cdot G_d^1(\vec{r}) d\vec{r} + \\ \int \vec{\nabla} G_s^1(\vec{r}) \cdot \delta D(\vec{r}) \cdot \vec{\nabla} G_d^1(\vec{r}) d\vec{r} \end{array} \right) \end{aligned}$$

where $G_s(r) = G(r_s, r)$ is the Green function representing photon density, at a point r of the medium MC when the medium MC is illuminated by the source s located at $r_s$, and $G_d(r) = G(r_d, r)$ is the Green function representing photon density at the point r of the medium MC when the medium MC is illuminated by the source s located at $r_d$.

In other words, $G_{sd}$ corresponds to the true values $\mu_a(r)$ and $D(r)$, and $G_{sd}^1$ corresponds to approximated values $\mu_a^1(r)$ and $D^1(r)$ with $\mu_a^1(r) = \mu_a(r) + \delta\mu_a(r)$ and $D^1(r) = D(r) + \delta D(r)$.

The operation of this example is otherwise similar to that of the example described previously and will not be further described.

The advantages of this example are similar to those of the example described previously and will not be further described.

The reconstruction of the optical properties $\mu_a(r)$ or $D(r)$ is then performed assuming either that $\delta\mu_a(\vec{r}) = 0$, or that $\delta D(\vec{r}) = 0$, using known inversion algorithms such as those mentioned previously.

According to one variant, the position of fluorophores is reconstructed in the medium to be characterized MC. For this purpose, a measurement $A_{sd}$ is carried out corresponding to excitation of the reference medium MR with the reference wavelength $\lambda_{ref}$. This reference wavelength corresponds to the excitation wavelength of the fluorophore $\lambda_{ex}$. The signal $A_{sd}$ is therefore detected at the excitation wavelength $\lambda_{ex}$. It is then assumed that the response of the detector $D_d$ undergoes negligible change between the excitation wavelength $\lambda_{ex}$ and the reference wavelength $\lambda_{ref}$, or that its trend is controlled for example via a relationship of proportionality. It is then assumed that the instrument response $IRF_{sd}^{\lambda_{ex}}$ corresponding to the detection performed at the excitation wavelength is related to the instrument response $IRF_{sd}^{\lambda_{em}}$ corresponding to the detection performed at the emission wavelength via a relationship of type $IRF_{sd}^{\lambda_{em}} = \alpha IRF_{sd}^{\lambda_{ex}}$, $\alpha$ being a positive scalar.

This measurement is performed on the reference medium MR whose optical properties are known. Preferably these are close to within a few ten percentages, for example to within 50% of those of the medium to be characterized MC.

$$A_{sd} = IRF_{sd}^{\lambda_{ex}} \cdot G_{sd}^0, \qquad (21)$$

$G_{sd}^0$ being the Green function corresponding to photon density at $\vec{r} = \vec{r}_d$, in the reference medium MR when this medium is illuminated by a point source at $\vec{r} = \vec{r}_s$ Each measurement $B_{sd}$ corresponds to the fluorescence signal, at the emission wavelength $\lambda_{em}$, measured by a detector d located at $r_d$, when the medium to be characterized MC is excited by an excitation source s, located at $r = r_s$, and exciting the medium at the excitation wavelength $\lambda_{ex}$.

Each measurement $B_{sd}$ is modeled as follows:

$$B_{sd} = IRF_{sd}^{\lambda_{em}} \cdot \int G_s^{\lambda_{ex}}(\vec{r}) \cdot F(\vec{r}) \cdot G_d^{\lambda_{em}}(\vec{r}) d\vec{r} \qquad (22)$$

With:

$G_s^{\lambda_{ex}}(\vec{r})$: Green function corresponding to photon density at $\vec{r}$ when the medium is illuminated by a point source at $\vec{r}_s$ $G_d^{\lambda_{em}}(\vec{r})$: Green unction corresponding to photon density at $\vec{r}_d$ when the medium is illuminated by a point source at $\vec{r}$ $F(\vec{r})$: response of the fluorophore located in the volume $d\vec{r}$, this function having been previously defined.

The corrected magnitude $Y_{sd}$ is then determined such that:

$$\begin{aligned} Y_{sd} &= B_{sd} \cdot G_{sd}^0 \qquad (23) \\ &= IRF_{sd}^{\lambda_{em}} \cdot \int G_s^{\lambda_{ex}}(\vec{r}) \cdot F(\vec{r}) \cdot G_d^{\lambda_{em}}(\vec{r}) d\vec{r} \cdot G_{sd}^0 \\ &= \alpha A_{sd} \cdot \int G_s^{\lambda_{ex}}(\vec{r}) \cdot F(\vec{r}) \cdot G_d^{\lambda_{em}}(\vec{r}) d\vec{r} \end{aligned}$$

The corrected magnitude $Y_{sd}(t)$ is then related to measured or known magnitudes $(\alpha, A_{sd}(t))$, to modeled magnitudes $G_s^{\lambda_{ex}}(\vec{r})$, $G_d^{\lambda_{em}}(\vec{r})$, and to the unknowns $F(\vec{r})$. By having several corrected magnitudes, corresponding to different source-detector pairs, the magnitudes $F(\vec{r})$ are reconstructed using known inversion algorithms such as those previously mentioned.

According to a third embodiment, in which elements identical to the first previously described embodiment carry identical reference numbers and are not further described, the reconstruction system 10 is a system having a frequency radiation source.

Each radiation source 14 is a frequency radiation source i.e. an intensity-modulated source at a given frequency. According to this variant each radiation source 14 comprises a laser source, for example intensity-modulated at radio frequencies i.e. frequencies of the order of a few hundred MHz.

Each detector 16 is a frequency detector and is capable of measuring the amplitude of the light intensity and its phase relative to the source 14.

According to embodiment further example, the first and second distributions are complex frequency distributions respectively denoted $A_{sd}(\omega)$ and $B_{sd}(\omega)$. The establishing means 42 are preferably in the form of software able to be stored in the memory 40.

According to the example, the first and second modeling functions and the corrected signal are respectively denoted $G_{sd}^{0}(\omega)$, $G_{sd}(\omega)$ and $Y_{sd}(\omega)$. These three functions are complex.

According to the further example, the product of the first distribution $A_{sd}(\omega)$ and the second modeling function $G_{sd}(\omega)$ and the product of the second distribution $B_{sd}(\omega)$ and first modeling function $G_{sd}^{0}(\omega)$ are multiplications, the first $A_{sd}(\omega)$ and second $B_{sd}(\omega)$ distributions being frequency distributions.

The arithmetical operation is for example a subtraction of the product of the first frequency distribution $A_{sd}(\omega)$ and the second modeling function $G_{sd}(\omega)$ from the product of the second frequency distribution $B_{sd}(\omega)$ and the first modeling function $G_{sd}^{0}(\omega)$.

The corrected signal $Y_{sd}(\omega)$ then verifies the following equation:

$$Y_{sd}(\omega) = B_{sd}(\omega) \cdot G_{sd}^{0}(\omega) - A_{sd}(\omega) \cdot G_{sd}(\omega) \qquad (24)$$

where $B_{sd}(\omega)$ is the second frequency distribution
$G_{sd}^{0}(\omega)$ is the first modeling function,
$A_{sd}(\omega)$ the first frequency distribution, and
$G_{sd}(\omega)$ is the second modeling function.

The operation of this embodiment is otherwise similar to that of the previously described examples and will not be further described.

The advantages of this third embodiment are similar to those of the previously described examples and will not be further described.

It will be therefore be appreciated that the reconstruction method and the reconstruction system 10 of the invention allow the reconstruction of desired optical properties whist not necessitating any experimental determination of instrument response.

The invention claimed is:

1. A method for reconstructing optical properties of a medium to be characterized, using a reconstruction system comprising at least one source-detector pair, each source detector pair comprising:
    a pulsed radiation source capable of illuminating a medium, and
    a time-resolved detector, capable of receiving a signal emitted by the medium,
the method comprising the following steps:
    providing a reference medium, with known optical properties;
    illuminating the reference medium by a pulsed radiation source of a source-detector pair;
    receiving a signal by the time-resolved detector of the source-detector pair, the received signal being emitted by the reference medium subsequent to the illumination of the reference medium by the pulsed radiation source and establishing a first time distribution of the signal received by the time-resolved detector;
    determining, for the source-detector pair, a first modeling function of a light scattering signal between the pulsed radiation source and the time-resolved detector in the reference medium;
    illuminating the medium to be characterized by the pulsed radiation source of the source-detector pair;
    receiving a signal by the time-resolved detector of the source-detector pair, the received signal being emitted by the medium to be characterized subsequent to the illumination of the medium to be characterized by the pulsed radiation source and establishing a second time distribution of the signal received by the time-resolved detector;
    determining, for the source-detector pair, a second modeling function of a light scattering signal between the pulsed radiation source and the time-resolved detector in the medium to be characterized;
    computing a corrected signal from the first time distribution, the first modeling function, the second time distribution and the second modeling function, wherein the computing step comprises a comparison operation of the product of the first time distribution and the second modeling function with the product of the second time distribution and the first modeling function; and
    using the corrected signal to reconstruct optical properties of the medium to be characterized to allow detection of a pathology.

2. The method according to claim 1, wherein the comparison operation comprises an arithmetical operation of the product of the first time distribution and the second modeling function with the product of the second time distribution and the first modeling function.

3. The method according to claim 2, wherein the arithmetical operation is a subtraction of the product of the first time distribution and the second modeling function from the product of the second time distribution and the first modeling function.

4. The method according to claim 2, wherein the arithmetical operation is a ratio between the product of the second time distribution and the first modeling function and the product of the first time distribution and the second modeling function.

5. The method according to claim 1, wherein the product of the first time distribution and the second modeling function and the product of the second time distribution and the first modeling function are convolution products.

6. The method according to claim 1, wherein the first time distribution is established for an excitation wavelength, the second time distribution is established for an emission wavelength, and
    wherein the corrected signal is expressed as a function of the product of a positive scalar and the first time distribution, the product of the second time distribution and the first modeling function being a function of the product of the positive scalar and the first time distribution, the positive scalar being equal to the ratio between an instrument response corresponding to the detection performed at the emission wavelength and an instrument response corresponding to the detection performed at the excitation wavelength.

7. The method according to claim 1, wherein the optical properties comprise at least one element from among the group consisting of:

the absorption properties of light, characterized in particular by the absorption coefficient, the scattering properties, characterized in particular by the reduced scattering coefficient or by the scattering coefficient, and the fluorescence properties, characterized in particular by a response function of a fluorophore, or by a concentration of the fluorophore, or by a magnitude that is function of a quantity of the fluorophore.

8. A method for reconstructing optical properties of a medium to be characterized, using a reconstruction system comprising at least one source-detector pair, each source detector pair comprising:

a continuous radiation source capable of illuminating a medium; and a continuous detector, capable of receiving a signal emitted by the medium;

the method comprising the following steps:

providing a reference medium, with known optical properties;

illuminating the reference medium by a continuous radiation source of a source-detector pair;

receiving a signal by the continuous detector of the source-detector pair, the received signal being emitted by the reference medium subsequent to the illumination of the reference medium by the continuous radiation source and establishing a first continuous distribution of the signal received by the continuous detector;

determining, for the source-detector pair, a first modeling function of a light scattering signal between the continuous radiation source and the continuous detector in the reference medium;

illuminating the medium to be characterized by the continuous radiation source of the source-detector pair;

receiving a signal by the continuous detector of the source-detector pair, the received signal being emitted by the medium to be characterized subsequent to the illumination of the medium to be characterized by the continuous radiation source and establishing a second continuous distribution of the signal received by the continuous detector;

determining, for the source-detector pair, a second modeling function of a light scattering signal between the continuous radiation source and the continuous detector in the medium to be characterized;

computing a corrected signal from the first modeling function, the second continuous distribution and the second modeling function, the first continuous distribution, wherein the computing step comprises a comparison operation of the product of the first continuous distribution and the second modeling function with the product of the second continuous distribution and the first modeling function; and using the corrected signal to reconstruct optical properties of the medium to be characterized to allow detection of a pathology.

9. The method according to claim 8, wherein the product of the first continuous distribution and the second modeling function and the product of the second continuous distribution and the first modeling function are multiplications.

10. The method according to claim 8, wherein the computing step further comprises:

an arithmetical operation of the product of the first continuous distribution and the second modeling function with the product of the second continuous distribution and the first modeling function, wherein the arithmetical operation is a subtraction of the product of the first continuous distribution and the second modeling function from the product of the second continuous distribution and the first modeling function.

11. The method according to claim 8, wherein the first continuous distribution is established for an excitation wavelength, the second continuous distribution is established for an emission wavelength, and wherein the corrected signal is expressed as a function of the product of a positive scalar and the first continuous distribution, the product of the second continuous distribution and the first modeling function being a function of the product of the positive scalar and the first continuous distribution, the positive scalar being equal to the ratio between an instrument response corresponding to the detection performed at the emission wavelength and an instrument response corresponding to the detection performed at the excitation wavelength.

12. The method according to claim 8, wherein the optical properties comprise at least one element from among the group consisting of:

the absorption properties of light, characterized in particular by the absorption coefficient, the scattering properties, characterized in particular by the reduced scattering coefficient or by the scattering coefficient, and the fluorescence properties, characterized in particular by a response function of a fluorophore, or by a concentration of the fluorophore, or by a magnitude that is function of a quantity of the fluorophore.

13. A method for reconstructing optical properties of a medium to be characterized, using a reconstruction system comprising at least one source-detector pair, each source detector pair comprising:

a frequency radiation source capable of illuminating a medium; and a frequency detector capable of receiving a signal emitted by the medium;

the method comprising the following steps:

providing a reference medium, with known optical properties;

illuminating the reference medium by a frequency radiation source of a source-detector pair;

receiving a signal by the frequency detector of the source-detector pair, the received signal being emitted by the reference medium subsequent to the illumination of the reference medium by the frequency radiation source and establishing a first frequency distribution of the signal received by the frequency detector;

determining, for the source-detector pair, a first modeling function of a light scattering signal between the frequency radiation source and the frequency detector in the reference medium;

illuminating the medium to be characterized by the frequency radiation source of the source-detector pair;

receiving a signal by the frequency detector of the source-detector pair, the received signal being emitted by the medium to be characterized subsequent to the illumination of the medium to be characterized by the frequency radiation source and establishing a second frequency distribution of the signal received by the frequency detector;

determining, for the source-detector pair, a second modeling function of a light scattering signal between the frequency radiation source and the frequency detector in the medium to be characterized;

computing a corrected signal from the first modeling function, the second frequency distribution and the second modeling function, the first frequency distribution, wherein the computing step comprises a comparison operation of the product of the first frequency distribution and the second modeling function with the product of the second frequency distribution and the first modeling function; and using the corrected signal to reconstruct optical properties of the medium to be characterized to allow detection of a pathology.

14. The method according to claim 13, wherein the product of the first frequency distribution and the second modeling function and the product of the second frequency distribution and the first modeling function are multiplications.

15. The method according to claim 13, wherein the computing step further comprises:

an arithmetical operation of the product of the first frequency distribution and the second modeling function with the product of the second frequency distribution and the first modeling function, wherein the arithmetical operation is a subtraction of the product of the first frequency distribution and the second modeling function from the product of the second frequency distribution and the first modeling function.

16. The method according to claim 13, wherein the first frequency distribution is established for an excitation wavelength, the second frequency distribution is established for an emission wavelength, and wherein the corrected signal is expressed as a function of the product of a positive scalar and the first frequency distribution, the product of the second frequency distribution and the first modeling function being a function of the product of the positive scalar and the first frequency distribution, the positive scalar being equal to the ratio between an instrument response corresponding to the detection performed at the emission wavelength and an instrument response corresponding to the detection performed at the excitation wavelength.

17. The method according to claim 13, wherein the optical properties comprise at least one element from among the group consisting of:

the absorption properties of light, characterized in particular by the absorption coefficient, the scattering properties, characterized in particular by the reduced scattering coefficient or by the scattering coefficient, and the fluorescence properties, characterized in particular by a response function of a fluorophore, or by a concentration of the fluorophore, or by a magnitude that is function of a quantity of the fluorophore.

* * * * *